(12) United States Patent
Rabizadeh

(10) Patent No.: US 11,702,703 B2
(45) Date of Patent: Jul. 18, 2023

(54) TARGETED CELL FREE NUCLEIC ACID ANALYSIS

(71) Applicant: NantHealth Labs, Inc., Culver City, CA (US)

(72) Inventor: Shahrooz Rabizadeh, Agoura Hills, CA (US)

(73) Assignee: NantHealth Labs, Inc., Culver City, CA (US)

( * ) Notice: Subject to any disclaimer, the term of this patent is extended or adjusted under 35 U.S.C. 154(b) by 367 days.

(21) Appl. No.: 16/759,577

(22) PCT Filed: Nov. 6, 2018

(86) PCT No.: PCT/US2018/059371
§ 371 (c)(1),
(2) Date: Apr. 27, 2020

(87) PCT Pub. No.: WO2019/094363
PCT Pub. Date: May 16, 2019

(65) Prior Publication Data
US 2020/0270705 A1    Aug. 27, 2020

Related U.S. Application Data

(60) Provisional application No. 62/582,619, filed on Nov. 7, 2017.

(51) Int. Cl.
| | | |
|---|---|---|
| *C12Q 1/68* | (2018.01) | |
| *C12Q 1/6886* | (2018.01) | |
| *G16B 5/00* | (2019.01) | |
| *C12Q 1/6806* | (2018.01) | |
| *C12Q 1/6853* | (2018.01) | |

(52) U.S. Cl.
CPC ......... *C12Q 1/6886* (2013.01); *C12Q 1/6806* (2013.01); *C12Q 1/6853* (2013.01); *G16B 5/00* (2019.02); *C12Q 2525/301* (2013.01); *C12Q 2531/113* (2013.01); *C12Q 2600/158* (2013.01); *C12Q 2600/178* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 8,304,187 B2 | 11/2012 | Fernando | |
| 9,422,592 B2 | 8/2016 | Morris et al. | |
| 2007/0072223 A1 | 3/2007 | Slepnev | |
| 2010/0209930 A1 | 8/2010 | Fernando | |
| 2012/0059670 A1 | 3/2012 | Sanborn et al. | |
| 2012/0066001 A1 | 5/2012 | Sanborn et al. | |
| 2013/0323740 A1 | 12/2013 | Hoon et al. | |
| 2016/0002717 A1 | 1/2016 | Lee et al. | |
| 2016/0032396 A1 | 2/2016 | Diehn et al. | |
| 2017/0145509 A1 | 5/2017 | Koh et al. | |
| 2020/0270705 A1* | 8/2020 | Rabizadeh | C12Q 1/6806 |

FOREIGN PATENT DOCUMENTS

| | | | |
|---|---|---|---|
| WO | 2016077709 A1 | 5/2016 | |
| WO | WO-2016077709 A1 * | 5/2016 | ........... C12Q 1/6806 |
| WO | 2019/094363 A2 | 5/2019 | |
| WO | 2019/094363 A3 | 8/2019 | |

OTHER PUBLICATIONS

Blondal et al., 2013. Assessing sample and miRNA profile quality in serum and plasma or other biofluids. Methods, 59(1), pp. S1-S6. (Year: 2013).*
Boivin et al., 2018. Simultaneous sequencing of coding and noncoding RNA reveals a human transcriptome dominated by a small number of highly expressed noncoding genes. Rna, 24(7), pp. 950-965. (Year: 2018).*
Kakimoto, Y., Tanaka, M., Kamiguchi, H., Ochiai, E. and Osawa, M., 2016. MicroRNA stability in FFPE tissue samples: dependence on GC content. PloS one, 11(9), e0163125 pp. 1-13. (Year: 2016).*
Kroh et al., 2010. Analysis of circulating microRNA biomarkers in plasma and serum using quantitative reverse transcription-PCR (qRT-PCR). Methods, 50(4), pp. 298-301. (Year: 2010).*
Kwok et al., 2015. Targeted detection of G-quadruplexes in cellular RNAs. Angewandte Chemie International Edition, 54(23), pp. 6751-6754. (Year: 2015).*
Kwok et al., 2016. rG4-seq reveals widespread formation of G-quadruplexstructures in the human transcriptome. Nature methods, 13(10), pp. 841-844. (Year: 2016).*
Kwok, C.K., Marsico, G. and Balasubramanian, S., 2018. Detecting RNA G-quadruplexes (rG4s) in the transcriptome. Cold Spring Harbor perspectives in biology, 10(7), p. a032284. (Year: 2018).*
Pandey, S., Agarwala, P. and Maiti, S., 2013. Effect of loops and G-quartets on the stability of RNA G-quadruplexes. The journal of physical chemistry B, 117(23), pp. 6896-6905. (Year: 2013).*
Pradervand et al., 2010. Concordance among digital gene expression, microarrays, and qPCR when measuring differential expression of microRNAs. Biotechniques, 48(3), pp. 219-222. (Year: 2010).*
Sahdev et al., 2007. Amplification of GC-rich genes by following a combination strategy of primer design, enhancers and modified PCR cycle conditions. Molecular and cellular probes, 21 (4), pp. 303-307. (Year: 2007).*
Takeshita et al., 2013. Serum microRNA expression profile: miR-1246 as a novel diagnostic and prognostic biomarker for oesophageal squamous cell carcinoma. British journal of cancer, 108(3), pp. 644-652. (Year: 2013).*
Turchinovich, A., Weiz, L. and Burwinkel, B., 2013. Isolation of circulating microRNA associated with RNA-binding protein. In Circulating MicroRNAs (pp. 97-107). Humana Press, Totowa, NJ. (Year: 2013).*

(Continued)

*Primary Examiner* — Teresa E Strzelecka
*Assistant Examiner* — Olayinka A Oyeyemi
(74) *Attorney, Agent, or Firm* — Martin Fessenmaier; Umberg Zipser LLP

(57) ABSTRACT

Methods of isolating cell free RNA from individual's bodily fluid and reliably obtain cell free RNA data are presented, preferably by use of high-stability portions and/or use of targeted small amplicons on the cell free RNA.

14 Claims, No Drawings

(56) References Cited

OTHER PUBLICATIONS

Yamada et al., 2014. Technical factors involved in the measurement of circulating microRNA biomarkers for the detection of colorectal neoplasia. PLoS One, 9(11), e112481 pp. 1-8. (Year: 2014).*

Zheng et al., 2014. Anchored multiplex PCR for targeted next-generation sequencing. Nature medicine, 20(12), pp. 1479-1484. (Year: 2014).*

Bolduc et al., 2010. In-depth sequencing of the siRNAs associated with peach latent mosaic viroid infection. BMC molecular biology, 11, pp. 1-8. (Year: 2010).*

Deigan et al., 2009. Accurate SHAPE-directed RNA structure determination. Proceedings of the National Academy of Sciences, 106(1), pp. 97-102. (Year: 2009).*

Lucks et al., 2011, Multiplexed RNA structure characterization with selective 2'-hydroxyl acylation analyzed by primer extension sequencing (SHAPE-Seq). Proc. Natl. Acad. Sci. USA 108, 11063-11068. (Year: 2011).*

Merino et al., 2005. RNA structure analysis at single nucleotide resolution by selective 2 '-hydroxyl acylation and primer extension (SHAPE). Journal of the American Chemical Society, 127(12), pp. 4223-4231. (Year: 2005).*

Watters et al., 2016. Characterizing RNA structures in vitro and in vivo with selective 2'-hydroxyl acylation analyzed by primer extension sequencing (SHAPE-Seq). Methods, 103, pp. 34-48. (Year: 2016).*

Williams, G.D., Chang, R.Y. and Brian, D.A., 1999. A phylogenetically conserved hairpin-type 3' untranslated region pseudoknot functions in coronavirus RNA replication. Journal of virology, 73(10), pp. 8349-8355. (Year: 1999).*

International Preliminary Report on Patentability received for PCT Application Serial No. PCT/US2018/059371 dated May 22, 2020, 09 pages.

Fernando et al., "Stabilization of cell-free RNA in blood samples using a new collection device", Clinical Biochemistry, 2012, vol. 45, pp. 1497-1502.

Wong et al., "Optimizing blood collection, transport and storage conditions for cell free DNA increases access to prenatal testing", Clinical Biochemistry, 2013, vol. 46, pp. 1099-1104.

Buske et al., "Triplexator: Detecting nucleic acid triple helices in genomic and transcriptomicdata", Genome Research, 2012, vol. 22, pp. 1372-1381.

Holland et al., "Structural features and stability of an RNA triple helix in solution", Nucleic Acids Research, 1996, vol. 24, No. 14, pp. 2841-2848.

Koberle et al., "Differential Stability of Cell-Free Circulating microRNAs: Implications for Their Utilization as Biomarkers", PLOS ONE, Sep. 2013, vol. 8, No. 9, pp. 11 pages.

Spornraft et al., "Optimization of Extraction of Circulating RNAs from Plasma-Enabling Small RNA Sequencing", PLOS ONE, Sep. 2014, vol. 9, No. 9, 11 pages.

White Douglas "Circulating Cell-Free Nucleic Acids: Characteristics, Purification and Applications", Promega, 2013, 40 pages.

International Search Report with International Application No. PCT/US2018/059371 dated Nov. 6, 2018, pp. 11.

* cited by examiner

TARGETED CELL FREE NUCLEIC ACID ANALYSIS

This application claims priority to our US provisional application having the Ser. No. 62/582,619, filed Nov. 7, 2017, which is incorporated by reference in its entirety herein.

FIELD OF THE INVENTION

The field of the invention is diagnostic methods in cancer therapy, especially as it relates to diagnosis, prognosis, and treatment of cancer using liquid biopsy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Genetic abnormalities or abnormal expression of genes are frequently associated with prognosis of many diseases including inflammatory diseases, autoimmune diseases, metabolic diseases, and various types of cancer. Most typically, the genetic abnormalities or abnormal expression of genes are determined by examining tissues and/or analyzing omics data of the tissues obtained by excisional or incisional biopsy. While excisional or incisional biopsy directly provide relevant tissue and cells from which omics data can be obtained, such procedures are often not desirable and may not be performed frequently due to the invasiveness and difficulties to gain access to the target tissue.

More recently, liquid biopsies using cell free (or free circulating) DNA and/or RNA populations in peripheral blood have become an at least conceptually simple method for the analysis of genetic abnormalities associated with prognosis of cancer. For example, U.S. Pat. No. 9,422,592 discloses the measurement of cell free RNA (cfRNA) of formulpeptide receptor gene (FPR1) and its association with the patient's risk for having lung cancer or non-small cell lung cancer (NSCLC). However, as the quantity of cell free RNA of specific gene of interest (e.g., a gene encoding tumor-specific epitope) is generally marginal in a limited volume of bodily fluid, and as cell free RNA tends to degrade rapidly, omics data on some cell free RNA may not be reliably obtained and analyzed. So far, most efforts have been made to solve the problem by increasing the overall yield of cell free RNAs during the purification step and by reducing the amount of RNA degradation using RNAase inhibitor or chemicals of similar functions. Yet, such approach may not be equally effective for all nucleic acids, and will not improve detection where RNA is already degraded in vivo.

Therefore, even though various methods of purification of RNA with reduced RNA degradation are known, individual gene-specific approach for reliably and stably obtaining and analyzing cell free RNA has been largely unexplored. Thus, there remains a need for improved methods for reliably and stably obtaining and analyzing cell free RNA.

SUMMARY OF THE INVENTION

The inventive subject matter is directed to various compositions and methods of isolating cell free RNA and reliably obtaining cell free RNA data at a desirable signal to noise ratio, even when the RNA is partially degraded. Thus, in one aspect of the inventive subject matter, the inventors contemplate a method of obtaining cell free RNA data. In this method, a sample containing cell free RNA from an individual is obtained. Preferably, the sample is a bodily fluid of the individual. Then, a high-stability portion of the cell free RNA is amplified to obtain the cell free RNA data, which includes at least one of RNA sequence data and the RNA expression level.

Preferably, the cell free RNA is derived from at least one of the following: a cancer-related gene, a cancer-specific gene, a DNA-repair gene, a neoepitope, and a gene not associated with a disease. In some embodiments, the neoepitope is tumor-specific and individual-specific. In other embodiments, the cell free RNA is a small noncoding RNA.

In some embodiments, the high-stability portion can be identified by length or structure of the portion, a location within the cell free RNA, an interaction of the high-stability portion with a protein, an empirical analysis of portions of the cell free RNA, and/or by in silico modeling of the cell free RNA. The structure of the portion may comprise at least one of a hairpin structure, a loop structure, a pseudoknot structure, and a bulge structure. The location may be within 200 base pairs from 5'-end of the cell free RNA. In some embodiments, the in silico modeling presents the predicted secondary structure in vivo or in vitro.

In some embodiments, amplifying a high-stability portion of the cell free RNA comprises amplifying fragments of the high-stability portion in different lengths. In such embodiments, it is preferred that the fragments are amplified in different lengths using a plurality of distinct 5'-primers or distinct 3'-primers.

In some embodiments, the RNA sequence data are selected from the group consisting of mRNA sequence data and splice variant data, and/or the RNA expression level data are selected from the group consisting of a quantity of RNA transcript and a quantity of a small noncoding RNA.

Another aspect of the inventive subject matter includes a method of isolating cell free RNA. In this method, a sample containing cell free RNA from an individual is obtained and subsequently contacted with a synthetic nucleic acid. Preferably, the synthetic nucleic acid is configured to bind to at least a portion of 5'-portion of the cell free RNA and form a cell free RNA-synthetic nucleic acid complex. Most typically, the sample is a bodily fluid of the individual. The so formed cell free RNA-synthetic nucleic acid complex is isolated and the method optionally can be continued with analyzing the cell free RNA associated with the synthetic nucleic acid or cell free RNA dissociated from the synthetic nucleic acid.

In some embodiments, the cell free RNA is derived from at least one of the following: a cancer-related gene, a cancer-specific gene, a DNA-repair gene, a neoepitope, and a gene not associated with a disease. Preferably, the neoepitope is tumor-specific and individual-specific. In other embodiments, cell free RNA is a small noncoding RNA.

In some embodiments, the synthetic nucleic acid is a double-stranded DNA, and the cell free RNA-synthetic nucleic acid complex is a DNA-RNA triplex. In other embodiments, the synthetic nucleic acid is a single-stranded DNA, and cell free RNA-synthetic nucleic acid complex is a DNA-RNA hybrid double helix.

In some embodiments, the synthetic nucleic acid is immobilized via at least one of a nanoparticle, a magnetic bead, a glass bead, a biotin bead, and a quantum dot, and/or is immobilized on the solid carrier via a covalent bonding to a surface of the solid carrier.

In some embodiments, the portion of the 5'-portion of the cell free RNA is within 500 or 200 base pairs from 5'-end of the cell free RNA. In other embodiments, the portion of the 5'-portion of the cell free RNA is within 150 or 120 base pairs from 5'-end of the cell free RNA.

In some embodiments, the step of isolating comprises separating the RNA-synthetic nucleic acid complex by at least one of a change in molecular weight and a conformational change. In other embodiments, the synthetic nucleic acid is labeled with a tag, and the step of isolating comprises separating the RNA-synthetic nucleic acid complex using the tag.

Additionally, the method may further comprise a step of amplifying the cell free RNA from the isolated cell free RNA-synthetic nucleic acid complex to obtain the cell free RNA data, wherein the cell free RNA data comprises at least one of RNA sequence data and RNA expression level data. In such embodiments, it is preferred that the RNA sequence data are selected from the group consisting of mRNA sequence data and splice variant data and/or the RNA expression level data are selected from the group consisting of a quantity of RNA transcript and a quantity of a small noncoding RNA.

Various objects, features, aspects and advantages of the inventive subject matter will become more apparent from the following detailed description of preferred embodiments.

DETAILED DESCRIPTION

The inventors discovered that cell free RNA omics data can be reliably obtained by identifying and amplifying a high-stability portion of the cell free RNA. Such amplified high-stability portion of the cell free RNA can be further analyzed to obtain cell free RNA sequence data and/or RNA expression level data. Viewed from a different perspective, the inventors discovered that primers for reliably amplifying a portion of cell free RNA can be designed and generated based on the identified high-stability portion of the cell free RNA. The inventors further discovered that the high-stability portion of the cell free RNA can be identified based on the length, structure, location, or any interaction of the portion with other molecules, which can be determined experimentally, empirically, or by in silico modeling. The inventors contemplate that such targeted amplification of cell free RNA sequences will improve the quality and reliability of the omics data by capturing cell free RNAs that may be relatively unstable and prone to degradation in vitro. Of course, it should be noted that RNA data are not necessarily limited to RNA, but may be represented as DNA sequence data where the analysis of the RNA included a step of reverse transcription.

As used herein, the term "tumor" refers to, and is interchangeably used with one or more cancer cells, cancer tissues, malignant tumor cells, or malignant tumor tissue, that can be placed or found in one or more anatomical locations in a human body. It should be noted that the term "patient" as used herein includes both individuals that are diagnosed with a condition (e.g., cancer) as well as individuals undergoing examination and/or testing for the purpose of detecting or identifying a condition. As used herein, the term "bind" refers to, and can be interchangeably used with a term "recognize" and/or "detect", an interaction between two molecules with a high affinity with a $K_D$ of equal or less than $10^{-6}$M, or equal or less than $10^{-7}$M. As used herein, the term "provide" or "providing" refers to and includes any acts of manufacturing, generating, placing, enabling to use, or making ready to use.

Cell-Free RNA

The inventors contemplate that an individual with a medical condition that is related to alteration of genes or gene expressions may be identified via liquid biopsy of the individual's bodily fluid or samples derived from the bodily fluid that may include cell free RNA. For example, treatment of a cancer patient with one or more cancer immunotherapy can trigger release of cell free RNA to the patient's bodily fluid, thus increase the quantity of specific types of the cell free RNA. As used herein, the individual's bodily fluid includes, but is not limited to, blood, serum, plasma, mucus, cerebrospinal fluid, ascites fluid, saliva, and urine of the individual. The individual's bodily fluid may be fresh or preserved/frozen.

As used herein, the cell free RNA may include any types of RNA that are circulating in the bodily fluid of an individual without being enclosed in a cell body or a nucleus. Most typically, the source of the cell free RNA is the cell directly or indirectly affected by the medical condition (e.g., cancer, etc.) or treatment to the medical condition (e.g., cancer immunotherapy). Thus, in one example, the source of the cell free RNA can be preferably a cancer cell. However, it is also contemplated that the source of the cell free RNA is the immune cell (e.g., NK cells, T cells, macrophages, etc.). Thus, where the medical condition is a tumor (or a cancer), the cell free RNA can be circulating tumor RNA (ctRNA) and/or cell free RNA (cfRNA, circulating nucleic acids that do not derive from a tumor). While not wishing to be bound by a particular theory, it is contemplated that the release of cell free RNA originated from the tumor cell can be increased when the tumor cell interact with the immune cell or when the tumor cells undergo cell death (e.g., necrosis, apoptosis, autophagy, etc.). Thus, in some embodiments, the cell free RNA may be enclosed in a vesicular structure (e.g., via exosomal release of cytoplasmic substances) so that it can be protected from RNase activity in some type of bodily fluid. Yet, it is also contemplated that in other embodiments, the cell free RNA is a naked RNA without being enclosed in any membranous structure, but may be stabilized via interaction with non-nucleotide molecules (e.g., any RNA binding proteins, etc.).

Therefore, in addition to quantification of any known cell free RNA, it is contemplated that the methods presented herein will also include quantification of any cell free RNA and/or specific fractions thereof to determine the presence of absence of a medical condition or the prognosis of the medical condition in the patient. Where specific fractions are quantified, it should be appreciated that such fractions may be particularly relevant to the specific disease. For example, especially suitable RNA fractions include those representing tumor associated genes and/or neoepitopes specific to a tumor in the patient (tumor-specific and/or patient-specific. Alternatively, or additionally, circulating RNA encoding DNA repair genes are also deemed suitable. As will be readily appreciated, such additional measurements may be used as a baseline and/or as an indicator of treatment efficacy. Examples for suitable methods are disclosed in co-pending U.S. provisional applications 62/504,149, filed May 10, 2017, 62/473,273, filed Mar. 17, 2017, and 62/500,497 filed May 3, 2017, all incorporated by reference herein.

It is contemplated that the cell free RNA can be any type of RNA which can be released from either cancer cells or immune cell. Thus, the cell free RNA may include mRNA, tRNA, microRNA, small interfering RNA, long non-coding RNA (lncRNA). Most typically, the cell free RNA is a full length or a fragment of mRNA (e.g., at least 70% of full-length, at least 50% of full length, at least 30% of full length, etc.) encoding one or more cancer-related proteins, inflammation-related proteins, cancer neoepitope (preferably patient-specific and tumor-specific). For example, the cell free mRNA are derived from the cancer related gene including, but not limited to, ABL1, ABL2, ACTB, ACVR1B, AKT1, AKT2, AKT3, ALK, AMER11, APC, AR, ARAF, ARFRP1, ARID1A, ARID1B, ASXL1, ATF1, ATM, ATR, ATRX, AURKA, AURKB, AXIN1, AXL, BAP1, BARD1, BCL2, BCL2L1, BCL2L2, BCL6, BCOR, BCORL1, BLM, BMPR1A, BRAF, BRCA1, BRCA2, BRD4, BRIP1, BTG1, BTK, EMSY, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEA, CEBPA, CHD2, CHD4, CHEK1, CHEK2, CIC, CREBBP, CRKL, CRLF2, CSF1R, CTCF, CTLA4, CTNNA1, CTNNB1, CUL3, CYLD, DAXX, DDR2, DEPTOR, DICER1, DNMT3A, DOT1L, EGFR, EP300, EPCAM, EPHA3, EPHA5, EPHA7, EPHB1, ERBB2, ERBB3, ERBB4, EREG, ERG, ERRFI1, ESR1, EWSR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLI1, FLT1, FLT3, FLT4, FOLH1, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HAVCR2, HGF, HMGB1, HMGB2, HMGB3, HNF1A, HRAS, HSD3B1, HSP90AA1, IDH1, IDH2, IDO, IGF1R, IGF2, IKBKE, IKZF1, IL7R, INHBA, INPP4B, IRF2, IRF4, IRS2, JAK1, JAK2, JAK3, JUN, MYST3, KDMSA, KDMSC, KDM6A, KDR, KEAP, KEL, KIT, KLHL6, KLK3, MLL, MLL2, MLL3, KRAS, LAG3, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUC1, MUTYH, MYC, MYCL, MYCN, MYD88, MYH, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX3, PAX, PBRM1, PDGFRA, PDCD1, PDCD1LG2, PDGFRB, PDK1, PGR, PIK3C2B, PIK3CA, PIK3CB, PIK3CG, PIK3R1, PIK3R2, PLCG2, PMS2, POLD1, POLE, PPP2R1A, PREX2, PRKAR1A, PRKC1, PRKDC, PRSS8, PTCH1, PTEN, PTPN11, QK1, RAC1, RAD50, RAD51, RAF1, RANBP1, RARA, RB1, RBM10, RET, RICTOR, RIT1, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, T (BRACHYURY), TAF1, TBX3, TERC, TERT, TET2, TGFRB2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, ZNF703, CD26, CD49F, CD44, CD49F, CD13, CD15, CD29, CD151, CD138, CD166, CD133, CD45, CD90, CD24, CD44, CD38, CD47, CD96, CD 45, CD90, ABCB5, ABCG2, ALCAM, ALPHA-FETOPROTEIN, DLL1, DLL3, DLL4, ENDOGLIN, GJA1, OVASTACIN, AMACR, NESTIN, STRO-1, MICL, ALDH, BMI-1, GLI-2, CXCR1, CXCR2, CX3CR1, CX3CL1, CXCR4, PON1, TROP1, LGR5, MSI-1, C-MAF, TNFRSF7, TNFRSF16, SOX2, PODOPLANIN, L1CAM, HIF-2 ALPHA, TFRC, ERCC1, TUBB3, TOP1, TOP2A, TOP2B, ENOX2, TYMP, TYMS, FOLR1, GPNMB, PAPPA, GART, EBNA1, EBNA2, LMP1, BAGE, BAGE2, BCMA, C10ORF54, CD4, CD8, CD19, CD20, CD25, CD30, CD33, CD80, CD86, CD123, CD276, CCL1, CCL2, CCL3, CCL4, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CCR1, CCR2, CCR3, CCR4, CCR5, CCR6, CCR7, CCR8, CCR9, CCR10, CXCL1, CXCL2, CXCL3, CXCLS, CXCL6, CXCL9, CXCL10, CXCL11, CXCL12, CXCL13, CXCL14, CXCL16, CXCL17, CXCR3, CXCR5, CXCR6, CTAG1B, CTAG2, CTAG1, CTAG4, CTAG5, CTAG6, CTAG9, CAGE1, GAGE1, GAGE2A, GAGE2B, GAGE2C, GAGE2D, GAGE2E, GAGE4, GAGE10, GAGE12D, GAGE12F, GAGE12J, GAGE13, HHLA2, ICOSLG, LAG1, MAGEA10, MAGEA12, MAGEA1, MAGEA2, MAGEA3, MAGEA4, MAGEA4, MAGEA5, MAGEA6, MAGEA7, MAGEA8, MAGEA9, MAGEB1, MAGEB2, MAGEB3, MAGEB4, MAGEB6, MAGEB10, MAGEB16, MAGEB18, MAGEC1, MAGEC2, MAGEC3, MAGED1, MAGED2, MAGED4, MAGED4B, MAGEE1, MAGEE2, MAGEF1, MAGEH1, MAGEL2, NCR3LG1, SLAMF7, SPAG1, SPAG4, SPAG5, SPAG6, SPAG7, SPAG8, SPAG9, SPAG11A, SPAG11B, SPAG16, SPAG17, VTCN1, XAGE1D, XAGE2, XAGE3, XAGE5, XCL1, XCL2, and XCR1. Of course, it should be appreciated that the above genes may be wild type or mutated versions, including missense or nonsense mutations, insertions, deletions, fusions, and/or translocations, all of which may or may not cause formation of full-length mRNA.

For another example, the cell free mRNA are those encoding a full length or a fragment of inflammation-related proteins, including, but not limited to, HMGB1, HMGB2, HMGB3, MUC1, VWF, MMP, CRP, PBEF1, TNF-α, TGF-β, PDGFA, IL-1, IL-2, IL-3, IL-4, IL-5, IL-6, IL-7, IL-8, IL-9, IL-10, IL-12, IL-13, IL-15, IL-17, Eotaxin, FGF, G-CSF, GM-CSF, IFN-γ, IP-10, MCP-1, PDGF, and hTERT, and in yet another example, the cell free mRNA encoded a full length or a fragment of HMGB1.

For still another example, the cell free mRNA are those encoding DNA-repair proteins, including, but not limited to, DNA glycosylase, APE1, XRCC1, PNKP, Tdp1, APTX, DNA polymerase β, FEN1, DNA polymerase δ or ε, PCNA-RFC, PARP, MutSα (MSH2-MSH6), MutSβ (MSH2-MSH3), MutLα (MLH1-PMS2), MutLβ (MLH1-PMS2), MutLγ (MLH1-MLH3), Exo1, PCNA-RFC, XPC-Rad23B-CEN2, UV-DDB (DDB1-XPE), CSA, CSB, TFIIH, XPB, XPD, XPA, RPA, XPG, ERCC1-XPF, DNA polymerase δ or ε, Mre11-Rad50-Nbs1, CtIP, RPA, Rad51, Rad52, BRCA1, BRCA2, Exo1, BLM-TopIIIα, GEN1-Yen1, Slx1-Slx4, Mus81/Eme1, and Ku70-Ku80, DNA-PKc, XRCC4-DNA ligase IV, XLF.

The cell free mRNA may be present in a plurality of isoforms (e.g., splicing variants, etc.) that may be associated with different cell types and/or location. Preferably, different isoforms of mRNA may be a hallmark of specific tissues (e.g., brain, intestine, adipose tissue, muscle, etc.), or may be a hallmark of cancer (e.g., different isoform is present in the cancer cell compared to corresponding normal cell, or the ratio of different isoforms is different in the cancer cell compared to corresponding normal cell, etc.). For example, mRNA encoding HMGB1 are present in 18 different alternative splicing variants and 2 unspliced forms. Those isoforms are expected to express in different tissues/locations of the patient's body (e.g., isoform A is specific to prostate, isoform B is specific to brain, isoform C is specific to spleen, etc.). Thus, in these embodiments, identifying the isoforms of cell free mRNA in the patient's bodily fluid can provide information on the origin (e.g., cell type, tissue type, etc.) of the cell free mRNA.

The inventors contemplate that the quantities and/or isoforms (or subtypes) or regulatory noncoding RNA (e.g., microRNA, small interfering RNA, long non-coding RNA (lncRNA), etc.) can vary and fluctuate by presence of a tumor or immune response against the tumor. Without wishing to be bound by any specific theory, varied expression of regulatory noncoding RNA in a cancer patient's bodily fluid may due to genetic modification of the cancer cell (e.g., deletion, translocation of parts of a chromosome, etc.), and/or inflammation at the cancer tissue by immune system (e.g., regulation of miR-29 family by activation of interferon signaling and/or virus infection, etc.). Thus, in some embodiments, the cell free RNA can be a regulatory noncoding RNA that modulates expression (e.g., downregulates, silences, etc.) of mRNA encoding a cancer-related protein or an inflammation-related protein (e.g., HMGB1, HMGB2, HMGB3, MUC1, VWF, MMP, CRP, PBEF1, TNF-$\alpha$, TGF-$\beta$, PDGFA, IL-1, IL-2, IL-3, IL-4, IL-5, IL-6, IL-7, IL-8, IL-9, IL-10, IL-12, IL-13, IL-15, IL-17, Eotaxin, FGF, G-CSF, GM-CSF, IFN-$\gamma$, IP-10, MCP-1, PDGF, hTERT, etc.).

It is also contemplated that some cell free regulatory noncoding RNA may be present in a plurality of isoforms or members (e.g., members of miR-29 family, etc.) that may be associated with different cell types and/or location. Preferably, different isoforms or members of regulatory noncoding RNA may be a hallmark of specific tissues (e.g., brain, intestine, adipose tissue, muscle, etc.), or may be a hallmark of cancer (e.g., different isoform is present in the cancer cell compared to corresponding normal cell, or the ratio of different isoforms is different in the cancer cell compared to corresponding normal cell, etc.). For example, higher expression level of miR-155 in the bodily fluid can be associated with the presence of breast tumor, and the reduced expression level of miR-155 can be associated with reduced size of breast tumor. Thus, in these embodiments, identifying the isoforms of cell free regulatory noncoding RNA in the patient's bodily fluid can provide information on the origin (e.g., cell type, tissue type, etc.) of the cell free regulatory noncoding RNA.

Isolation of Cell Free RNA

Any suitable methods to isolate cell free RNA are contemplated. Most typically, cell free RNA is isolated from a bodily fluid (e.g., whole blood, serum, etc.) or any sample that may contain cell free RNA of the individual that is processed under conditions that stabilize cell free mRNA. In some embodiments, the bodily fluid of the patient can be obtained from a patient before and after the cancer immunotherapy. While it may vary depending on the type of cancer immunotherapy and/or the type of cancer, the bodily fluid of the patient can be obtained at least 24 hours, at least 3 days, at least 7 days after the cancer immunotherapy. For more accurate comparison, the bodily fluid from the patient before the cancer immunotherapy can be obtained less than 1 hour, less than 6 hours before, less than 24 hours before, less than a week before the beginning of the cancer immunotherapy. In addition, a plurality of samples of the bodily fluid of the patient can be obtained during a period before and/or after the cancer immunotherapy (e.g., once a day after 24 hours for 7 days, etc.).

Additionally or alternatively, the bodily fluid of a healthy individual can be obtained to compare the quantity and/or subtype expression of cell free RNA. As used herein, a healthy individual refers an individual without a tumor. Preferably, the healthy individual can be chosen among group of people shares characteristics with the patient (e.g., age, gender, ethnicity, diet, living environment, family history, etc.).

In more detail, suitable tissue sources include whole blood, which is preferably provided as plasma or serum. Alternatively, it should be noted that various other bodily fluids are also deemed appropriate so long as cell free RNA is present in such fluids. Appropriate fluids include saliva, ascites fluid, spinal fluid, urine, etc., which may be fresh or preserved/frozen. For example, for the analyses presented herein, specimens were accepted as 10 ml of whole blood drawn into cell-free RNA BCT® tubes or cell-free DNA BCT® tubes containing RNA stabilizers, respectively. Advantageously, cell free RNA is stable in whole blood in the cell-free RNA BCT tubes for seven days while cell free RNA is stable in whole blood in the cell-free DNA BCT Tubes for fourteen days, allowing time for shipping of patient samples from world-wide locations without the degradation of cell free RNA. Moreover, it is generally preferred that the cell free RNA is isolated using RNA stabilization agents that will not or substantially not (e.g., equal or less than 1%, or equal or less than 0.1%, or equal or less than 0.01%, or equal or less than 0.001%) lyse blood cells. Viewed from a different perspective, the RNA stabilization reagents will not lead to a substantial increase (e.g., increase in total RNA no more than 10%, or no more than 5%, or no more than 2%, or no more than 1%) in RNA quantities in serum or plasma after the reagents are combined with blood. Likewise, these reagents will also preserve physical integrity of the cells in the blood to reduce or even eliminate release of cellular RNA found in blood cell. Such preservation may be in form of collected blood that may or may not have been separated. In less preferred aspects, contemplated reagents will stabilize cell free RNA in a collected tissue other than blood for at 2 days, more preferably at least 5 days, and most preferably at least 7 days. Of course, it should be recognized that numerous other collection modalities are also deemed appropriate, and that the cell free RNA can be at least partially purified or adsorbed to a solid phase to so increase stability prior to further processing.

As will be readily appreciated, fractionation of plasma and extraction of cell free RNA can be done in numerous manners. In one exemplary preferred aspect, whole blood in 10 mL tubes is centrifuged to fractionate plasma at 1600 rcf for 20 minutes. The so obtained plasma is then separated and centrifuged at 16,000 rcf for 10 minutes to remove cell debris. Of course, various alternative centrifugal protocols are also deemed suitable so long as the centrifugation will not lead to substantial cell lysis (e.g., lysis of no more than 1%, or no more than 0.1%, or no more than 0.01%, or no more than 0.001% of all cells). Cell free RNA is extracted from 2 mL of plasma using Qiagen reagents. The extraction protocol was designed to remove potential contaminating blood cells, other impurities, and maintain stability of the nucleic acids during the extraction. All nucleic acids were kept in bar-coded matrix storage tubes, with DNA stored at −4° C. and RNA stored at −80° C. or reverse-transcribed to cDNA that is then stored at −4° C. Notably, so isolated cell free RNA can be frozen prior to further processing.

Alternatively, the inventors contemplate that some cell free RNAs can be targeted and isolated from other cell free RNAs by providing a synthetic or recombinant nucleic acid that can bind to the cell free RNA. Any suitable synthetic or recombinant nucleic acids that can bind and stabilize the cell free RNA are contemplated. For example, the synthetic or recombinant nucleic acid can be a double-stranded DNA that has complementary sequences with the cell free RNA. As used herein, the complementary sequences includes any sequences that can stably bind to the cell free RNA. Thus, the complementary sequences may include sequences fully complementary to the cell free RNA, at least 95% complementary, at least 90% complementary, at least 80% complementary, or at least 70% complementary to the cell free RNA. In this example, the cell free RNA may bind near or within the major groove of the double-stranded DNA to form a RNA-DNA triplex, at least partially. For another example, the synthetic or recombinant nucleic acid can be a single-stranded DNA that has complementary sequences with the cell free RNA, which can, together, form a DNA-RNA hybrid double helix, at least partially. Without wishing to be bound by any specific theory, the inventors contemplate that so formed RNA-DNA triplex or DNA-RNA hybrid double helix may protect the cell free RNA from RNase-mediated degradation or any other mechanism by which single-stranded RNA are more vulnerable to be degraded.

Preferably, the synthetic or recombinant nucleic acid includes nucleic acid sequences complementary to at least 20%, preferably at least 30%, more preferably at least 50% of length of the cell free RNA. In addition, while any portion of the cell free RNA may bind to the synthetic or recombinant nucleic acid, it is generally preferred that the synthetic or recombinant nucleic acid may include nucleic acid sequences complementary to at least a portion of first one fifth (⅕) of 5'-portion of the cell free RNA, first one fourth (¼) of 5'-portion of the cell free RNA, or first one third (⅓) of 5'-portion of the cell free RNA. For example, where the expected length of the cell free RNA is 150 base pairs (bps), the synthetic or recombinant nucleic acid includes may include nucleic acid sequences complementary to the 30 bps at 5'-end of cell free RNA (e.g., base pair number 1-30 from 5'-end, base pair number 10-40 from 5'-end, base pair number 20-50 from 5'-end, etc.) having a total length of 150 bps.

In a further preferred embodiment, the synthetic or recombinant nucleic acid may be immobilized on a solid carrier so that the cell free RNA bound to the synthetic or recombinant nucleic acid can be immobilized as well. Any suitable solid carrier can be used including, but not limited to, any planar substrate, a chip, a column, a bead, a dipstick-type format. Preferably, the synthetic or recombinant nucleic acid can be immobilized by at least one end (5'-end or 3'-end) of the synthetic or recombinant nucleic acid. Alternatively, the synthetic or recombinant nucleic acid may be immobilized on a solid carrier via any portion of the synthetic or recombinant nucleic acid (e.g., any nucleotide or nucleic acid in between the 5'-end and 3'-end).

In some embodiments, the synthetic or recombinant nucleic acid can be immobilized on the solid carrier by covalent bonding with the substrate on the carrier. For example, where the substrate is coated with a chemical having an aldehyde, the 5'-end of the synthetic or recombinant nucleic acid can form a covalent bonding with the aldehyde group via Schiff base bond. In other embodiments, the synthetic or recombinant nucleic acid can be coupled with a particle via which the synthetic or recombinant nucleic acid are immobilized on the solid carrier. Any suitable particles that can immobilize the nucleic acid include, but not limited to, a nanoparticle (e.g., a metal nanoparticle, etc.), a magnetic bead, a glass bead, a biotin bead, a quantum dot, or any other suitable materials. For example, a double-stranded synthetic DNA can be coupled with a magnetic bead at its 5-end, and immobilized on the surface via magnetic force applied from outside of the solid carrier or from the substrate on the surface of the solid carrier. For other example, a single-stranded synthetic DNA can be coupled with magnetic beads at each of its 5'-end and 3'-end such that the 5'-end and 3'-end of the single-stranded synthetic DNA can be immobilized in a different parts of the solid carrier (e.g., across the diameter of a capillary column, etc.).

In those embodiments where the synthetic or recombinant nucleic acid are immobilized on the solid carrier, the inventors contemplate that a sample (e.g., serum, blood, etc.) of an individual containing cell free RNA can be contacted with the synthetic or recombinant nucleic acid on the solid carrier so that the some cell free RNA having a complementary sequence with the synthetic or recombinant nucleic acid can be bound and immobilized on the solid carrier. Then, the unbound cell free RNA or other substances can be washed away to isolate the cell free RNA of interest from other nucleic acids in the sample. Thus, the inventors further contemplate that the solid carrier can include immobilized synthetic or recombinant nucleic acids having different complementary sequences targeting different cell free RNAs in an array such that a plurality of different cell free RNAs can be isolated from a single reaction (contact) of the sample with the solid carrier.

Additionally and alternatively, the synthetic or recombinant nucleic acid may be coupled with a nanoparticle or a bead as described above, but may not be immobilized on the solid carrier surface. In this embodiment, the synthetic or recombinant nucleic acid coupled with a nanoparticle or a bead as described can be free floating in a liquid buffer in a container (e.g., a column, a dish, a capillary, etc.). The sample can be contacted with the synthetic or recombinant nucleic acids in the buffer to form a triplex or DNA-RNA hybrid double helix, which can then be isolated from the other non-bound cell free RNAs or other substances in the sample using the nanoparticle or a bead as a tag (e.g., pull down the magnetic bead-associated nucleic acids using magnetic force, etc.).

The inventors further contemplate that the synthetic or recombinant nucleic acid bound to the cell free RNA should have higher molecular weight than other unbound synthetic or recombinant nucleic acid. Alternatively or additionally, the conformations of the synthetic or recombinant nucleic acid may be changed due to the binding to the cell free RNA. Thus, in some embodiments, the synthetic or recombinant nucleic acid bound to cell free RNA can be separated from the other unbound synthetic or recombinant nucleic acid by molecular weight-based separation (e.g., gel-electrophoresis, capillary-electrophoresis, etc.) or any other separation method that separates out molecules of different conformations (e.g., non-denaturing gel electrophoresis, etc.).

Selection of Area and Primers for Amplification

After isolation of the cell free RNA, cell free RNA are then amplified to quantify the expression level of the cell free RNA or analyzing its sequences. One of the common challenges in amplifying the isolated cell free RNA is that the cell free RNA often cannot be effectively amplified due to its tendency of degradation such that the quantification of so generated amplicon may not provide a reliable reflection of the quantity of cell free RNA present in the sample. The inventors found that amplicons of the cell free RNA can be more effectively and reliably generated using primers that target one or more relatively stable, or high-stability portions of the cell free RNA. As used herein, the relatively stable, or high-stability portion of the cell free RNA refers sequences in the cell free RNA that tends to be secured or protected from degradation in vitro and/or in vivo for at least 3 hours, 6 hours, 12 hours, 24 hours, or 3 days after generation of the cell free RNA or for at least 5 min, at least 15 min, at least 30 min, at least 1 hour, or at least 6 hours in vitro in a temperature of or higher than 4 degree Celsius.

Thus, in order to generate amplicons of the portion of cell free RNAs for reliable analysis, it is preferred to identify one or more high-stability portion of the cell free RNA. The inventors contemplate that a portion with a longer nucleic acid sequence length is less likely to provide a reliable amount and quality of amplicons as the longer nucleic acid may tend to degrade from its 3'-end (e.g., via 3'-5'-exonuclease, etc.). Thus, it is further contemplated that a portion with a shorter nucleic acid sequence length can be more stably and reliably transcribed than a portion with a longer nucleic acid sequence length a high-stability portions of the cell free RNA can be identified by a length of the portion. Based on this, it is contemplated that a high-stability portion of the cell free RNA can be any portion with a length less than 200 bps, preferably less than 150 bps, more preferably less than 120 bps, and even more preferably less than 100 bps. Thus, in one embodiment, the high-stability portion of the cell free RNA can be identified based on a length of the portion, and 5'- or 3'-primer for amplifying cell free RNA can be selected to amplify no more than 200 bps, preferably no more than 150 bps, more preferably no more than 120 bps, and even more preferably no more than 100 bps within the cell free RNA. In other word, 5'- or 3'-primer for amplifying cell free RNA can be selected based on the distance from the 3'- or 5'-primer, respectively.

Additionally, or alternatively, the inventors also contemplate that a portion of the cell free RNA at or near 3'-end is less likely to provide a reliable amount and quality of amplicons as the 3'-end of the nucleic acid is more vulnerable to the RNase-mediated degradation (e.g., via 3'-5'-exonuclease, etc.). Thus, it is further contemplated that a portion at 5'-end or near the 5'-end of the cell free RNA may be more stably and reliably transcribed than a portion at 3'-end or near the 3'-end of the cell free RNA. Thus, in one embodiment, the high-stability portion of the cell free RNA can be identified based on a location of the portion, and 5'- or 3'-primer for amplifying cell free RNA can be selected, designed, and/or generated to amplify no more than 300 bps, preferably no more than 200 bps, or 150 bps, or 120 bps, more preferably no more than 100 bps away from the 5'-end of the cell free RNA. In other word, 5'- or 3'-primer for amplifying cell free RNA can be selected, designed, and/or generated to amplify a portion of the cell free RNA located within 300 bps, preferably 200 bps, more preferably 100 bps from the 5'-end of the cell free RNA. Consequently, primers for amplification can be located towards the 5'-end of an RNA molecule (e.g., within the first 50% or within the first 40% or within the first 30% or within the first 20% of bases of the transcript) and selected, designed, and/or generated such that the amplicon has a length of equal or less than 200 bp, or equal or less than 150 bp, equal or less than 120 bp, equal or less than 100 bp, equal or less than 80 bp, or equal or less than 60 bp.

The inventors also contemplate that a portion of the cell free RNA forming a secondary structure is more likely to provide a reliable amount and quality of amplicons as the secondary structure of RNA provides structural stability so that it can be less vulnerable to degradation. Thus, in one embodiment, the high-stability portion of the cell free RNA can be identified based on a known secondary structure of the portion, which includes, but not limited to a stem-loop structure, a hairpin structure, a loop structure, a pseudoknot structure, and a bulge structure. Where the secondary structure of the cell free RNA is not experimentally determined or known, the secondary structure can be predicted via in silico modeling of the nucleic acid structure. Typically, the in silico modeling of the secondary structure calculates structures of the RNA by optimizing the thermodynamic free energy based on a nearest neighbor energy model. In this embodiment, 5'- or 3'-primer for amplifying cell free RNA can be selected, designed, and/or generated to amplify the sequences forming the secondary structure or a fragment thereof, or a portion of the cell free RNA including sequences forming the secondary structure and extra nucleic acids next to the secondary structure. Preferably, the extra nucleic acids amplified with the sequences forming the secondary structure is less than 50 bps, preferably less than 30 bps, more preferably less than 20 bps in either 5'- or 3'- of the secondary structure or both.

The inventors further contemplate that a portion of the cell free RNA interacting and/or binding to a protein (e.g., an RNA-binding protein except RNase) is more likely to provide a reliable amount and quality of amplicons as the RNA-protein interaction or binding provides structural stability and protection from RNase activity so that such portion can be less vulnerable to degradation. Thus, in one embodiment, the high-stability portion of the cell free RNA can be identified based on a known protein-interaction sequence in the cell free RNA. Where there is no known protein-interaction sequence in the cell free RNA, a protein-interaction sequence can be predicted by identifying any similar or consensus sequences in the cell free RNA to known protein-interaction sequence in other RNAs. In this embodiment, 5'- or 3'-primer for amplifying cell free RNA can be selected, designed, and/or generated to amplify the sequences within the protein-interaction sequence or a fragment thereof, or a portion of the cell free RNA including protein-interaction sequence and extra nucleic acids next to the protein-interaction sequence. Preferably, the extra nucleic acids amplified with the protein-interaction sequence is less than 50 bps, preferably less than 30 bps, more preferably less than 20 bps in either 5'- or 3'- of the protein-interaction sequence or both.

The inventors further contemplate that a high-stability portion of the cell free RNA that are relatively resistant to common RNA degradation mechanism may tend to survive in samples of other individuals. Thus, in one embodiment, the high-stability portion of the cell free RNA can be identified based on the empirical study of cell free RNAs detected in other samples from individuals with similar physical and medical conditions (e.g., age, gender, health status, diseases, disease prognosis, etc.), which can be typically conducted by analyzing omics data of individuals (e.g., by incrementally producing amplicons along a known transcript). In this embodiment, 5'- or 3'-primer for amplifying cell free RNA can be selected, designed, and/or generated to amplify frequently found fragment of the cell free RNA, or a fragment no further than 100 bps, preferably less than 50 bps, more preferably less than 20 bps from the end of the frequently found fragment.

Thus, in preferred aspect of the inventive subject matter, the inventors contemplate a method of obtaining cell free RNA data. In this method, a sample containing cell free RNA from an individual is obtained. Preferably, the sample is a bodily fluid of the individual. Then, the method continues with a step of identifying or ascertaining a high-stability portion of the cell free RNA. In some embodiments, the high-stability portion of the cell free RNA can be identified by determining a length of a portion of the cell free RNA that are preferably less than 200 bps, preferably less than 150 bps, more preferably less than 120 bps, and even more preferably less than 100 bps. In other embodiments, the high-stability portion of the cell free RNA can be identified by determining a location of a portion of the cell free RNA that are preferably within 300 bps, preferably 200 bps, more preferably 100 bps from the 5'-end of the cell free RNA, and/or within the first 50% or within the first 40% or within the first 30% or within the first 20% of bases of the transcript. In still other embodiments, the high-stability portion of the cell free RNA can be identified by determining a secondary structure of a portion of the cell free RNA that includes, but not limited to, a stem-loop structure, a hairpin structure, a loop structure, a pseudoknot structure, and a bulge structure. In still other embodiments, the high-stability portion of the cell free RNA can be identified by determining a portion of the cell free RNA interacting and/or binding to a protein. Such portion(s) of the cell free RNA (by length, by location, by secondary structure, by molecule interaction) can be determined by any suitable experimental methods including pull-down assay and/or RNA sequencing.

In still other embodiments, the high-stability portion of the cell free RNA can be ascertained based on the empirical study of cell free RNAs detected in other samples from individuals with similar physical and medical conditions (e.g., age, gender, health status, diseases, disease prognosis, etc.), which can be typically conducted by analyzing omics data of individuals (e.g., by incrementally producing amplicons along a known transcript). In this embodiment, 5'- or 3'-primer for amplifying cell free RNA can be selected, designed, and/or generated to amplify frequently found fragment of the cell free RNA, or a fragment no further than 100 bps, preferably less than 50 bps, more preferably less than 20 bps from the end of the frequently found fragment. In still other embodiments, the high-stability portion of the cell free RNA can be ascertained by in silico modeling of the nucleic acid structure (for secondary structure of RNA), and/or by in silico analysis of RNA sequence data of cell free RNA. Additionally and/or alternatively, the high-stability portion of the cell free RNA can be ascertained by a priori known and/or implicated high-stability portion of the cell free RNA that can be that can be obtained from a transcriptomics database.

Once a high-stability portion of the cell free RNA is selected or identified, the high-stability portion and/or the portion nearby can be amplified using a plurality sets of 5'- and/or 3'-primers to obtain a plurality sets of amplicons to determine the consistency between the absolute or relative quantities of the amplicons. For example, where the high-stability portion of the cell free RNA has a length of 100 bps, a 5'-primer for amplifying the high-stability portion can be selected, designed, and/or generated to be complementary to the 5'-end of the high-stability portion, and a plurality of 3'-primer can be selected, designed, and/or generated to be complementary to the different sub-portion of the high-stability portion such that the size of expected amplicons are, for example, 100 bps, 90 bps, 80 bps, 70 bps, etc. In another example, the 3'-primer for amplifying the high-stability portion can be selected, designed, and/or generated to be complementary to the 3'-end of the high-stability portion, and a plurality of 5'-primer can be selected, designed, and/or generated to be complementary to the different sub-portion of the high-stability portion such that the size of expected amplicons are, for example, 100 bps, 90 bps, 80 bps, 70 bps, etc. In still another example, a plurality of 5'-primers and 3'-primers can be paired to generate amplicons in different sizes. The inventors contemplate that such approach can reduce the possibility of false negative results of presence of the cell free RNA, and may further provide the most desired primer sets to amplify the specific cell free RNA that can provide amplicons most reliably and stably.

Amplification of Cell Free RNA and Analysis of Cell Free RNA Data

Once the high-stability portion of the cell free RNA is identified and desired primers to amplify the high-stability portion are designed and/or generated, various cell free RNA data can be obtained from quantification and/or sequence analysis of the cell free RNA. With respect to RNA sequence data, it should be noted that contemplated RNA sequence data includes mRNA sequence data, splice variant data, polyadenylation information, and any other suitable data obtained from sequencing of RNA molecules. Moreover, it is generally preferred that the RNA sequence data can be provided along with a metric for the transcription strength (e.g., number of transcripts of a damage repair gene per million total transcripts, number of transcripts of a damage repair gene per total number of transcripts for all damage repair genes, number of transcripts of a damage repair gene per number of transcripts for actin or other household gene RNA, etc.), and for the transcript stability (e.g., a length of poly A tail, etc.). Of course, and as noted above, the RNA data may be obtained by way of DNA where reverse transcription was employed. Thus, DNA data also represent RNA data.

With respect to the transcription strength (expression level), transcription strength of the cell free RNA can be examined by quantifying the cell free RNA. Quantification of cell free RNA can be performed in numerous manners, however, expression of analytes is preferably measured by quantitative real-time RT-PCR of cell free RNA using primers specific for each gene. For example, amplification can be performed using an assay in a 10 µL reaction mix containing 2 µL cell free RNA, primers, and probe. mRNA of α-actin can be used as an internal control for the input level of cell free RNA. A standard curve of samples with known concentrations of each analyte was included in each PCR plate as well as positive and negative controls for each gene. Test samples were identified by scanning the 2D barcode on the matrix tubes containing the nucleic acids. Delta Ct (dCT) was calculated from the Ct value derived from quantitative PCR (qPCR) amplification for each analyte subtracted by the Ct value of actin for each individual patient's blood sample. Relative expression of patient specimens is calculated using a standard curve of delta Cts of serial dilutions of Universal Human Reference RNA set at a gene expression value of 10 (when the delta CTs were plotted against the log concentration of each analyte).

Alternatively, where discovery or scanning for new mutations or changes in expression of a particular gene is desired, real time quantitative PCR may be replaced by RNAseq to so cover at least part of a patient transcriptome. Moreover, it should be appreciated that analysis can be performed static or over a time course with repeated sampling to obtain a dynamic picture without the need for biopsy of the tumor or a metastasis.

Such obtained RNA sequence data and/or quantification data comprises omics data of cell free RNA. The sequence data sets may include unprocessed or processed data sets, and exemplary data sets include those having BAM format, SAM format, FASTQ format, or FASTA format. However, it is especially preferred that the data sets are provided in BAM format or as BAMBAM diff objects (see e.g., US2012/0059670A1 and US2012/0066001A1). Moreover, the omics data of the individual can be compared with other individuals or healthy individuals to so obtain patient and tumor specific information. Further, so obtained omics information can then be processed using pathway analysis (especially using PARADIGM) to identify any impact of any mutations on cancer-related genes, neoepitope genes, or any genes that may be mutated or differentially expressed in relation to any medical conditions.

Likewise, computational analysis of the sequence data may be performed in numerous manners. In most preferred methods, however, analysis is performed in silico by location-guided synchronous alignment of cell free RNA of the patient and a healthy individual as, for example, disclosed in US 2012/0059670A1 and US 2012/0066001A1 using BAM files and BAM servers. Such analysis advantageously reduces false positive data and significantly reduces demands on memory and computational resources.

With respect to the analysis of cell free RNA of the patient and a healthy individual, numerous manners are deemed suitable for use herein so long as such methods will be able to generate a differential sequence object. However, it is especially preferred that the differential sequence object is generated by incremental synchronous alignment of BAM files representing genomic sequence information of the cell free DNA/RNA of the patient and a healthy individual. For example, particularly preferred methods include BAM-BAM-based methods as described in US 2012/0059670 and US 2012/0066001.

The inventors further contemplate that such obtained RNA sequence data and/or quantification data can be further used to select and/or generate more reliable treatment regimen to treat the patient, and further to administer such treatment regimen (e.g., cell-based therapy, chemotherapy, radiotherapy, vaccination, etc.) to the patient. For example, where such obtained RNA sequence data and/or quantification data indicates an emergence of a tumor-specific and individual-specific neoepitope (with a specific mutation detected from the sequence data) that are expressed by the tumor cells, the treatment regimen may include a vaccine composition (e.g., a viral vaccine, a bacterial vaccine, a yeast vaccine, etc.) comprising a recombinant nucleic acid encoding the neoepitope. Consequently, the patient can be administered with the vaccine composition in a dose and schedule effective to treat the tumor (e.g., to reduce the tumor size, to increase the immune response against the tumor, to increase the survival rate, etc.). In another example, where such obtained RNA sequence data and/or quantification data indicates overexpression of checkpoint-related genes (e.g., PD-L1, CTLA-4, TIM3, LAG3, etc.), the treatment regimen may include a checkpoint inhibitor (e.g., nivolumab, pembrolizumab, etc.). Consequently, the patient can be administered with the checkpoint inhibitor(s) in a dose and schedule effective to treat the tumor (e.g., to reduce the tumor size, to increase the immune response against the tumor, to increase the survival rate, etc.). In still another example, where such obtained RNA sequence data and/or quantification data indicates overexpression of specific types of chemokines/cytokines that inhibits the immune response in the tumor microenvironment, and/or proliferation or (hyper)activation of inhibitory immune cells (e.g., MDSC, Treg cells, etc.) in the tumor microenvironment, the treatment regimen may include an antibody or a recombinant molecule having a binding motif to the cytokines/chemokines and/or a cell-based therapy (e.g., genetically modified NK/NKT cells expressing Fas ligand and/or CD40 ligand, etc.) inducing cell death of such inhibitory immune cells or changing the tumor microenvironment to less immune-suppressive. Conversely, where such obtained RNA sequence data and/or quantification data indicates underexpression of specific types of chemokines/cytokines that enhance or elicit immune response, the treatment regimen may include immune stimulatory cytokine(s) (e.g., IL-2, IL-8, etc.) and a chemokine (e.g., CXCL14, CD40L, CCL2, CCL1, CCL22, CCL17, CXCR3, CXCL9, CXCL10, CXCL11, CXCL14, etc.) or any recombinant molecule including one or more of such immune stimulatory cytokine(s).

As used herein, the term "administering" refers to both direct and indirect administration of the treatment regimens, drugs, therapies contemplated herein, where direct administration is typically performed by a health care professional (e.g., physician, nurse, etc.), while indirect administration typically includes a step of providing or making the compounds and compositions available to the health care professional for direct administration.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

The invention claimed is:

1. A method of obtaining cell free RNA data, comprising:
    obtaining a sample containing cell free RNA from an individual;
    identifying a high-stability portion of the cell free RNA, wherein the high-stability portion comprises at least one of a hairpin structure, a loop structure, a pseudoknot structure, and a bulge structure, and wherein the high stability portion is located within 200 base pairs from 5'-end of the cell free RNA; and
    amplifying a high-stability portion of the cell free RNA to obtain the cell free RNA data, wherein the cell free RNA data comprises at least one of RNA sequence data and RNA expression level.

2. The method of claim 1, wherein the sample is a bodily fluid of the individual.

3. The method of claim 1, wherein the cell free RNA is derived from at least one of the following: a cancer-related gene, a cancer-specific gene, a DNA-repair gene, a neoepitope, and a gene not associated with a disease.

4. The method of claim 3, wherein the neoepitope is tumor-specific and individual-specific.

5. The method of claim 1, wherein the cell free RNA is a small noncoding RNA.

6. The method of claim 1, wherein the high-stability portion is identified by a length of the portion.

7. The method of claim 1, wherein the high-stability portion is identified by an interaction of the high-stability portion with a protein.

8. The method of claim 1, wherein the high-stability portion is identified by an empirical analysis of portions of the cell free RNA frequently found in samples from other than the individual.

9. The method of claim 1, wherein the high-stability portion is identified by in silica modeling of a predicted secondary structure of the cell free RNA.

10. The method of claim 9, wherein the in silica modeling present the predicted secondary structure in vivo or in vitro.

11. The method of claim 1, wherein amplifying comprises amplifying fragments of the high-stability portion in different lengths.

12. The method of claim 11, wherein the fragments are amplified in different lengths using a plurality of distinct 5'-primers or distinct 3'-primers.

13. The method of claim 1, wherein the RNA sequence data are selected from the group consisting of mRNA sequence data and splice variant data.

14. The method of claim 1, wherein the RNA expression level data are selected from the group consisting of a quantity of RNA transcript and a quantity of a small noncoding RNA.

* * * * *